US008705781B2

(12) United States Patent
Holmberg

(10) Patent No.: US 8,705,781 B2
(45) Date of Patent: Apr. 22, 2014

(54) OPTIMAL SPATIAL FILTERING IN THE PRESENCE OF WIND IN A HEARING PROSTHESIS

(75) Inventor: Paul Holmberg, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 71 days.

(21) Appl. No.: 13/289,753

(22) Filed: Nov. 4, 2011

(65) Prior Publication Data
US 2013/0114835 A1 May 9, 2013

(51) Int. Cl.
H04R 25/00 (2006.01)

(52) U.S. Cl.
USPC .......................................... 381/313; 381/317

(58) Field of Classification Search
USPC ............. 381/312–331, 13, 23.1, 56–57, 94.1, 381/356–359
See application file for complete search history.

(56) References Cited

U.S. PATENT DOCUMENTS

| 6,272,229 | B1 * | 8/2001 | Baekgaard | 381/313 |
| 6,882,736 | B2 | 4/2005 | Dickel et al. | |
| 7,881,480 | B2 * | 2/2011 | Buck et al. | 381/94.1 |
| 8,098,844 | B2 | 1/2012 | Elko | |
| 8,280,086 | B2 * | 10/2012 | Topholm | 381/315 |
| 8,374,366 | B2 * | 2/2013 | Kidmose | 381/313 |
| 2004/0165736 | A1 | 8/2004 | Hetherington et al. | |
| 2012/0148067 | A1 * | 6/2012 | Petersen et al. | 381/92 |

OTHER PUBLICATIONS

Tammara Stender & Marcel Hielsher; "Windguard: Bringing Listening Comfort to Windy Conditions"; ReSound; Sep. 2011.

* cited by examiner

Primary Examiner — Brian Ensey
Assistant Examiner — Norman Yu
(74) Attorney, Agent, or Firm — McDonnell Boehnen Hulbert & Berghoff LLP

(57) ABSTRACT

The present application discloses methods, systems, and hearing prostheses for reducing wind noise and/or thermal noise in an audio signal transmitted to the user of a hearing prosthesis. A method in accordance with the present disclosure includes utilizing delay-sum beamforming to improve the signal-to-noise ratio in an audio signal that contains wind noise and/or thermal noise. In the presence of at least one of wind noise and thermal noise, amplitudes and phases of at least two input signals are matched. The two signals are then added together, resulting in an average improvement in the signal-to-noise ratio of the signal transmitted to the user of about 3 dB.

19 Claims, 6 Drawing Sheets

OPTIMAL SPATIAL FILTERING IN THE PRESENCE OF WIND IN A HEARING PROSTHESIS

BACKGROUND

Various types of hearing prostheses provide persons having different kinds of hearing loss with the ability to perceive sound. Hearing loss may be conductive, sensorineural, or some combination of conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound directly or indirectly to a person's bone or teeth, thereby causing vibrations in the person's inner ear and bypassing the person's auditory canal and middle ear. Vibration-based hearing devices include, for example, bone-anchored devices, direct acoustic stimulation devices, or other vibration-based devices. A bone-anchored device typically utilizes a surgically implanted mechanism or a passive connection through the skin or teeth to transmit vibrations corresponding to sound via the skull. A direct acoustic stimulation device also typically utilizes a surgically implanted mechanism to transmit vibrations corresponding to sound, but bypasses the skull and more directly stimulates the inner ear. Other non-surgical vibration-based hearing devices may use similar vibration mechanisms to transmit sound via direct or indirect vibration of teeth or other cranial or facial bones.

Persons with certain forms of sensorineural hearing loss may benefit from prostheses, such as cochlear implants and/or auditory-brain-stem implants. For example, cochlear implants can provide a person having sensorineural hearing loss with the ability to perceive sound by stimulating the person's auditory nerve via an array of electrodes implanted in the person's cochlea. A component of the cochlear implant detects sound waves, which are converted into a series of electrical stimulation signals that are delivered to the implant recipient's cochlea via the array of electrodes. Auditory-brain-stem implants can use technology similar to cochlear implants, but instead of applying electrical stimulation to a person's cochlea, auditory-brain-stem implants apply electrical stimulation directly to a person's brain stem, bypassing the cochlea altogether. Electrically stimulating auditory nerves in a cochlea with a cochlear implant or electrically stimulating a brain stem may enable persons with sensorineural hearing loss to perceive sound. Further, some persons may benefit from hearing prostheses that combine one or more characteristics of the acoustic hearing aids, vibration-based hearing devices, cochlear implants, and auditory-brain-stem implants to enable the person to perceive sound.

To improve the quality of audio signals received by the user of a hearing prosthesis, it is desirable to use directional audio transducers, such as directional microphones.

SUMMARY

Directional audio transducers are susceptible to wind noise and thermal noise (e.g. microphone noise), the presence of which may make hearing difficult or unpleasant for the user of the hearing prosthesis. Therefore, it is preferred to use omnidirectional audio transducers and to filter wind noise and/or thermal noise from an audio signal before the audio signal is transmitted to the user of the hearing prosthesis. It is preferable, moreover, to not filter audio signals, regardless of the direction of their respective sources, while doing so and to not effectively disable any audio transducers otherwise in use by the hearing prosthesis when wind noise is detected. The present application discloses methods, systems, and hearing prostheses for filtering wind noise and thermal noise from sound signals received by a hearing prosthesis. The hearing prosthesis may be a cochlear implant, a bone-anchored device, a direct acoustic stimulation device, an auditory-brain-stem implant, an acoustic hearing aid, or any other device suitable for allowing an individual with hearing loss to perceive sound. Preferred embodiments described herein utilize delay-sum beamforming to reduce wind noise and/or thermal noise in audio signals received by components of the hearing prosthesis.

Some embodiments are directed to a method that includes utilizing delay-sum beamforming to reduce the level of wind noise and/or thermal noise before transmitting an audio signal to the user of a hearing prosthesis. In one example, an audio signal is received by a first audio transducer before it is received by a second audio transducer. The received audio signals are then filtered in order to match their amplitudes and phases. In one example, a time delay is then inserted into the audio signal received by the first audio transducer. The matched audio signals are then added together. The summation of the two signals may result in an increase in the amplitude of correlated signals (e.g. audio signals) of about 6 dB on average and an increase in the amplitude of uncorrelated signals (e.g. noise) of about 3 dB on average. The resulting combined audio signal is then transmitted to the user of the hearing prosthesis.

Other embodiments are directed to a system in which at least one or more processors detect the presence of at least one of wind noise and thermal noise in two or more audio signals. If the one or more processors do not detect at least one of wind noise and thermal noise, then the one or more sound processor processes audio signals in a normal (or default) mode. However, if the one or more processors detect at least one of wind noise and thermal noise, then the one or more processors employ a delay-sum beamforming mode for processing signals.

In yet other embodiments, a hearing prosthesis comprises two or more audio transducers, at least one processor, and an output component. The at least one processor receives audio signals from the at least two audio transducers. The at least two audio transducers may be omnidirectional microphones, a combination of directional microphone(s) and omnidirectional microphone(s), and/or any audio transducer(s) suitable for use in a hearing prosthesis. If the at least one processor detects at least one of wind noise and thermal noise in the audio signals received from the at least two audio transducers, the processor utilizes delay-sum beamforming to reduce the amount of wind noise and/or thermal noise in the audio signal sent to the user of the hearing prosthesis. This allows the hearing prosthesis to utilize all of the at least two audio transducers without sacrificing performance in the presence of wind noise and/or thermal noise.

In still other embodiments, instructions for matching the amplitudes and the phases of each input signal received from each audio transducer of a hearing prosthesis are stored in a non-transitory computer-readable medium accessible by at least one processor. When implementing a delay-sum beamforming mode of processing audio signals, the at least one processor implements instructions for matching the amplitudes and the phases of each input signal received from each audio transducer. In some embodiments, the at least one processor dynamically determines which audio transducer is farthest away from the target source. In these alternative embodiments, the at least one processor dynamically assigns time delays to each audio transducer except the audio transducer determined to be farthest from the target source.

In further embodiments, after implementing a delay-sum beamforming mode of processing audio signals, at least one processor outputs a combination of matched input signals to an output filter to at least partially reduce and/or remove wind noise and/or thermal noise from the combination of matched input signals. The filtered-combination signal is then sent to additional components of the hearing prosthesis so that the user may perceive the audio signal as sound.

In addition, some aspects of the disclosed methods may be performed by circuitry configured to perform logical functions in any of the processes or methods described herein. In still further examples, many types of devices may be used or configured to perform logical functions in any of the processes or methods described herein. In yet further examples, many types of devices (and/or components or sub-components of the devices) may be used or configured as means for performing functions of any of the methods described herein (or any portions of the methods described herein).

DETAILED DESCRIPTION OF DRAWINGS

The following detailed description describes various features, functions, and attributes of the disclosed systems, methods, and hearing prostheses with reference to the accompanying figures. In the figures, similar symbols typically identify similar components, unless context dictates otherwise. The illustrative embodiments described herein are not meant to be limiting. Certain aspects of the disclosed systems, methods, and hearing prostheses can be arranged and combined in a wide variety of different configurations, all of which are contemplated herein.

Figure 1A:
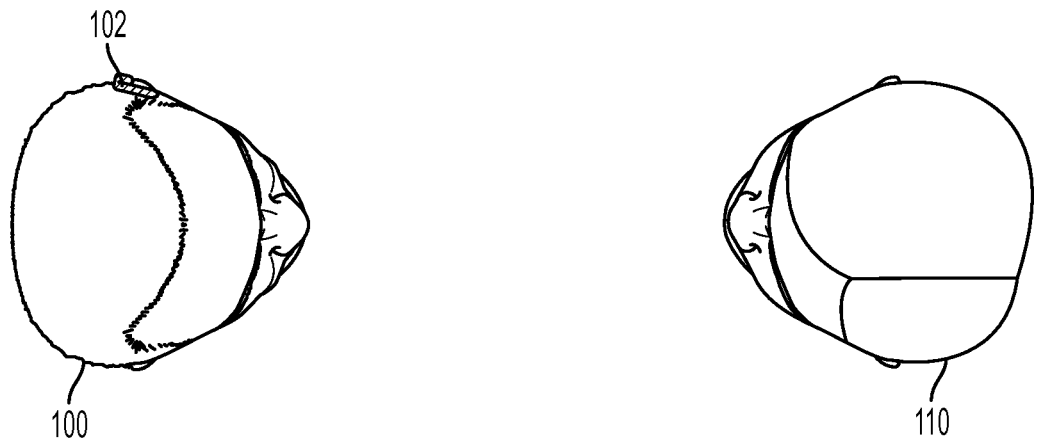
FIG. 1A is a conceptual diagram illustrating the spatial orientation of a user of a hearing prosthesis with a target source.
Figure 1B:
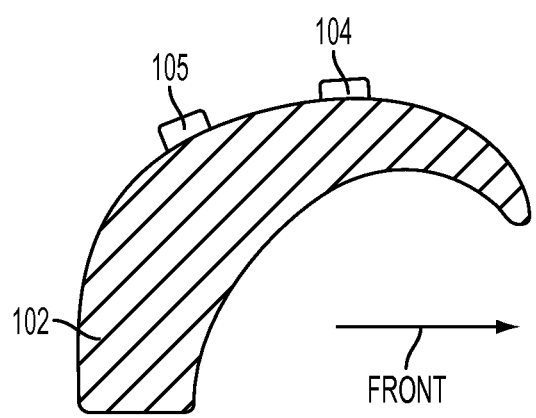
FIG. 1B is a side profile of an embodiment of the hearing prosthesis utilized in FIG. 1A, in which the positioning of audio transducers on the hearing prosthesis is shown.

In a first example, consider a user who suffers from hearing loss. To alleviate this condition, the user utilizes a hearing prosthesis, which may be a cochlear implant, a bone-conduction device, an auditory-brain-stem implant, a direct acoustic stimulation device, a hearing aid, or the like. In FIG. 1A, a user 100 utilizes a hearing prosthesis 102, which is depicted as part of a cochlear implant. In the illustrative example, the hearing prosthesis 102 has two microphones, with a first microphone 104 being located forward of a second microphone 105 on the hearing prosthesis 102, as depicted in FIG. 1B.

In the example illustrated in FIG. 1A, the first microphone 104 and the second microphone 105 are omnidirectional microphones. The omnidirectional microphones 104, 105 receive sounds from the environment, which include sounds emitted from a target source 110. In FIG. 1A, the target source 110 is a person centered in front of the user 100 at a distance of about 1 meter, which is a typical distance between two people engaging in conversation. However, in other embodiments the target source 110 is at a location other than the location depicted in FIG. 1A. Additionally, the target source 110 can be anything emitting a sound on which the user 100 would desire to focus his hearing. For example, the target source 110 may be a stereo speaker at a specific distance behind the user 100 or at some distance to the side of the user 100. In yet other embodiments, the location of the target source 110 may change dynamically.

In some situations, the presence of wind noise may interfere with the ability of the first microphone 104 and the second microphone 105 to adequately and comfortably supply sound from the environment to the user. In other situations, the complete absence of noise (e.g. the user is in a large, empty auditorium) results in the user hearing thermal noise radiated from the first microphone 104 and the second microphone 105. Both situations can make hearing difficult or uncomfortable for the user 100. Embodiments of the present invention reduce such unwanted wind noise and/or thermal noise through the use of delay-sum beamforming without having to forego or compromise the use of any microphones (e.g., the first microphone 104 and the second microphone 105) (or other audio transducers) of a hearing prosthesis 102.

Delay-sum beamforming provides a means for increasing the amplitude of correlated signals. For example, consider a two-microphone system in which the microphones have identical magnitude and phase responses. One microphone is closer to a target source than the other microphone is. Thus, a sound wave emitted from the target source will arrive at the closer microphone first. In order to match the phases of the received signals, a time delay is applied to the audio signal received by the closer of the two microphones, with the time delay being dependent upon the speed of sound, the distance between the two microphones, and the arrival angle of the sound. When the delay is applied to the audio signal received by the closer of the two microphones, the audio signals from both microphones are synchronized. Adding the two signals together has the effect of doubling the amplitude of the correlated signals, which equates to an average increase in amplitude of about 6 dB. However, the amplitude of uncorrelated signals increases by an average of about 3 dB. Thus, the resulting signal-to-noise ratio (SNR) may be, on average, 3 dB, thereby improving the quality of the audio signal and making it easier to distinguish uncorrelated signals (e.g. wind noise and/or thermal noise) from correlated signals (audio signals emitted from the target source).

Figure 2:
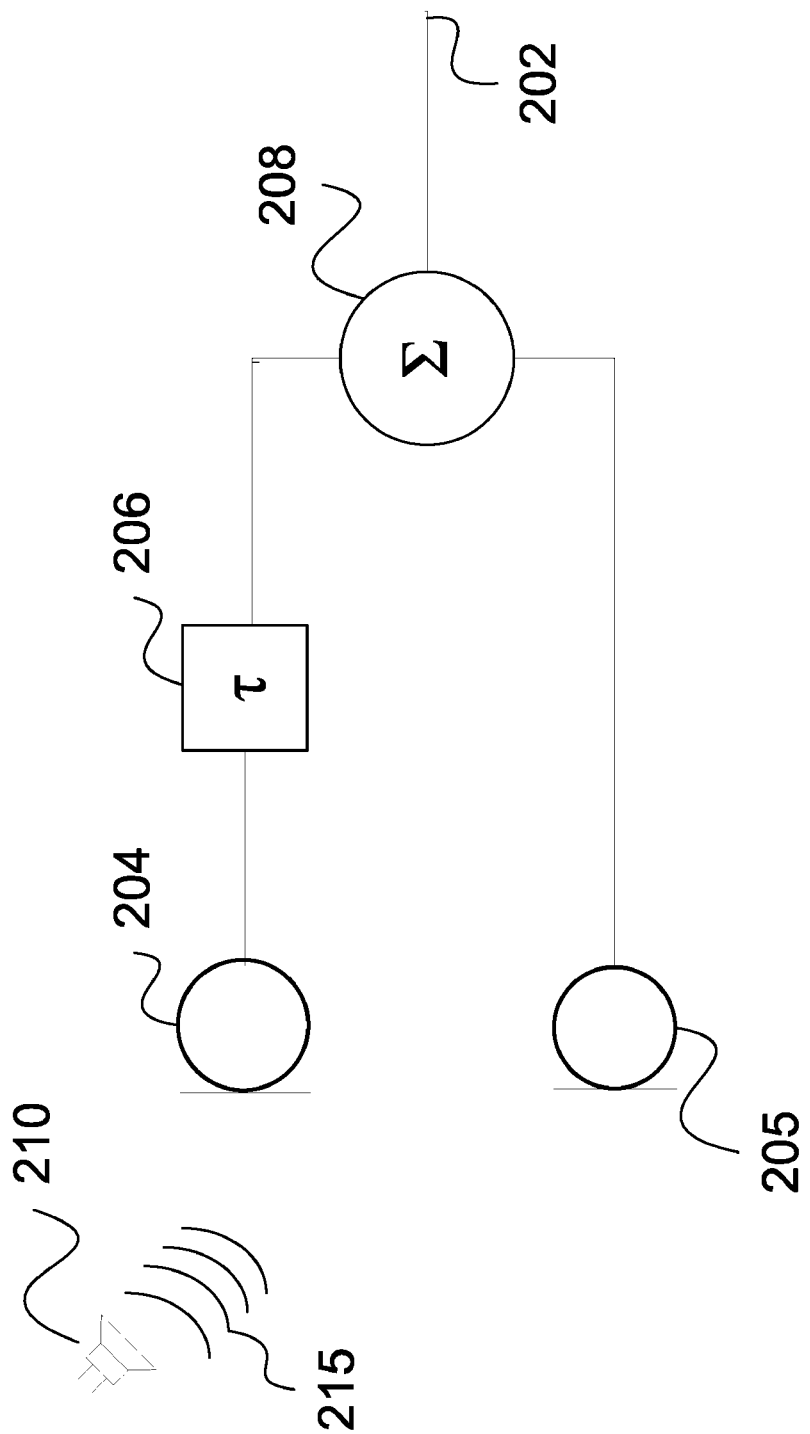
FIG. 2 is a simplified block diagram illustrating delay-sum beamforming for removing at least one of wind noise and thermal noise according to some embodiments of the present invention.

FIG. 2 shows a simplified block diagram 200 of one embodiment of the present invention. A first audio transducer 204 and a second audio transducer 205 receive an audio signal 215 from a target source 210. In this embodiment, first audio transducer 204 and second audio transducer 205 have identical amplitude and phase responses. Since the target source 210 is located closer to the first audio transducer 204 than to the second audio transducer 205, the audio signal arrives at the first audio transducer 204 before it arrives at the second audio transducer 205.

In the presence of at least one of wind noise and/or thermal noise, both audio transducers 204, 205 will receive uncorrelated noise. In order to reduce the unwanted noise from the output signals transmitted to the user, a time delay 206 is applied to a first input signal supplied by the first audio transducer 204. In some embodiments, the value of the time delay 206 is determined by the following formula:

$$\tau = (d \times \cos(\theta)) \div v$$

with d being the distance between the first audio transducer 204 and the second audio transducer 205, $\theta$ being the arrival angle of the audio signal emitted from the target source 210 to the first audio transducer 204 in the horizontal plane, and v being the speed of sound.

In the presently illustrated embodiment, in which the target source 210 is centered about 1 meter in front of the user of the hearing prosthesis, d is about 0.01 meters, and $\theta$ is about 0°. However, in other examples and embodiments, d may be up to about 0.1 meters depending on the type of hearing prosthesis utilized. Similarly, $\theta$ may be any angle between 0° and 90° depending on the location of the target source 210 relative to the user and the first audio transducer 204. For example, if the target source 210 is abreast of the user and first audio transducer 204, $\theta$ is about 90°. In other embodiments, the target source 210 is behind the user, in which case audio signals arrives at the second audio transducer 205 before the first audio transducer 204. In this arrangement, the time delay is applied to a second input signal supplied by the second audio transducer 205, and $\theta$ is the arrival angle of the audio signal to the second audio transducer 205 in the horizontal plane. Returning to the present embodiment, using a speed of sound of about 340 meters per second results in the time delay 206 equaling about 29 microseconds.

Once the time delay 206 is applied to the first input signal, the delayed first input signal is synchronized with the second input signal (i.e. the amplitudes and the phases of both signals are matched). The two input signals are then combined by an adding algorithm 208. The combined signal is then transferred to an output 202 for further processing and delivery to the user.

Figure 3:
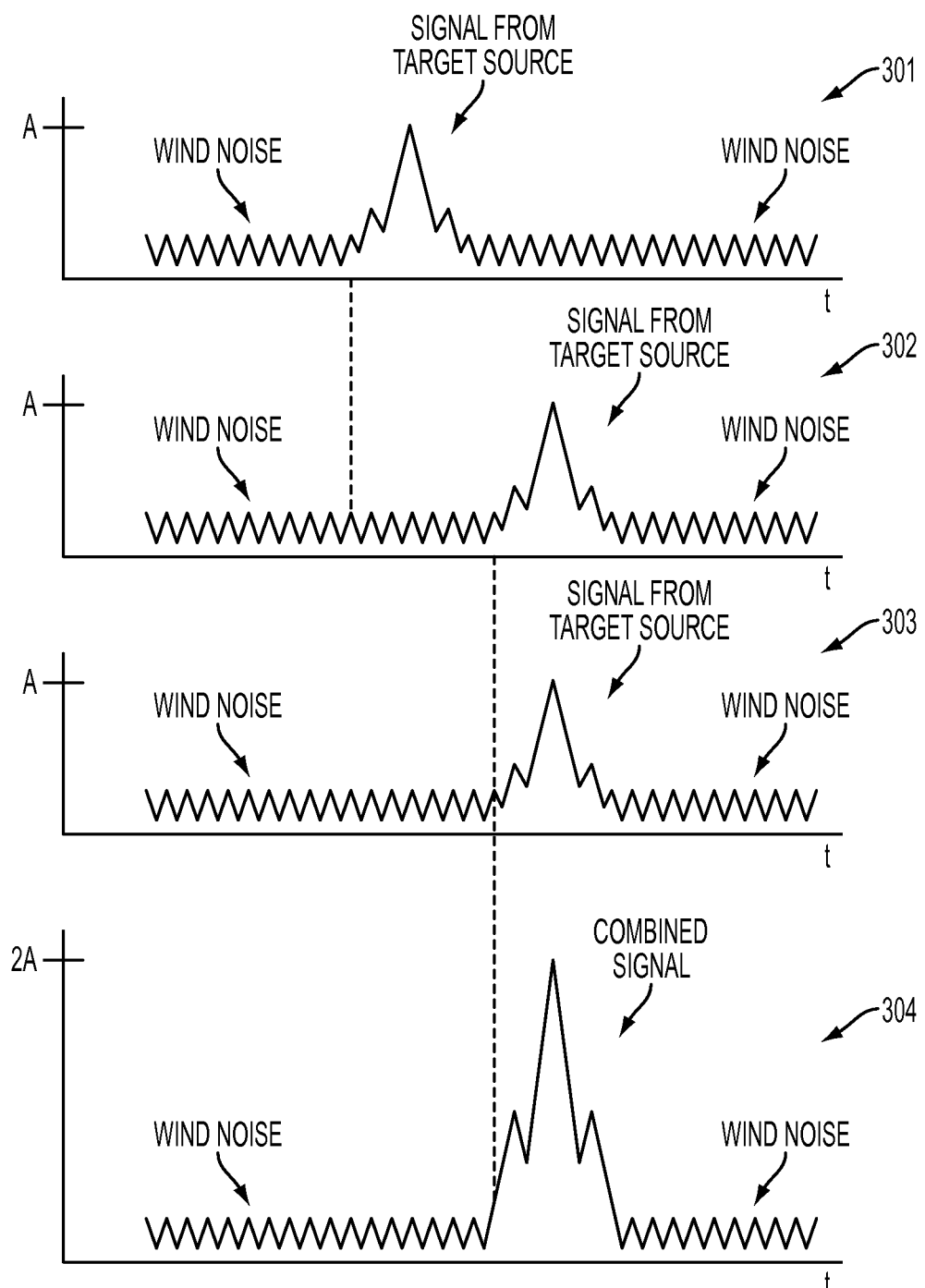
FIG. 3 depicts the waveforms of an audio signal in a system that implements one embodiment of the present invention.

With reference to FIG. 2, FIG. 3 illustrates the effect of delay-sum beamforming on audio signals received by the first audio transducer 204 and the second audio transducer 205. The first audio transducer 204 and the second audio transducer 205 receive an audio signal from the target source 210. Graph 301 shows an input signal as supplied by the first audio transducer 204 versus time, and graph 302 shows the same input signal as supplied by the second audio transducer 205 versus time. Wind noise is also received by both the first audio transducer 204 and the second audio transducer 205. Because the first audio transducer 204 is closer to the target source 210 than the second audio transducer 205 is, the first audio transducer 204 receives the audio signal first. Thus, the peaks corresponding to the audio signal occur earlier in graph 301 than in graph 302. In this example, both input signals have a maximum amplitude of A.

Graph 303 represents the delayed first input signal. The time delay 206 has the effect of shifting the input signal to the right on the time axis, thereby causing the delayed first input signal in graph 303 to be synchronized with the second input signal in graph 302. Graph 304 shows the result of combining the second input signal in graph 302 with the delayed first input signal in graph 303 via the adding algorithm 208. Because the signals are correlated and synchronized, the resulting waveform for the combined audio signal has a new maximum amplitude of about 2 A, which is about a 6 dB increase.

The amplitude of the noise received from both audio transducers 204, 205 also increases, on average, in graph 304 when compared to graphs 302 and 303. However, because the noise is uncorrelated, the resulting average increase in amplitude is only about 3 dB. Thus, using delay-sum beamforming to process the audio signal results in an improvement in the signal-to-noise ratio (SNR) of, on average, about 3 dB.

Figure 4:
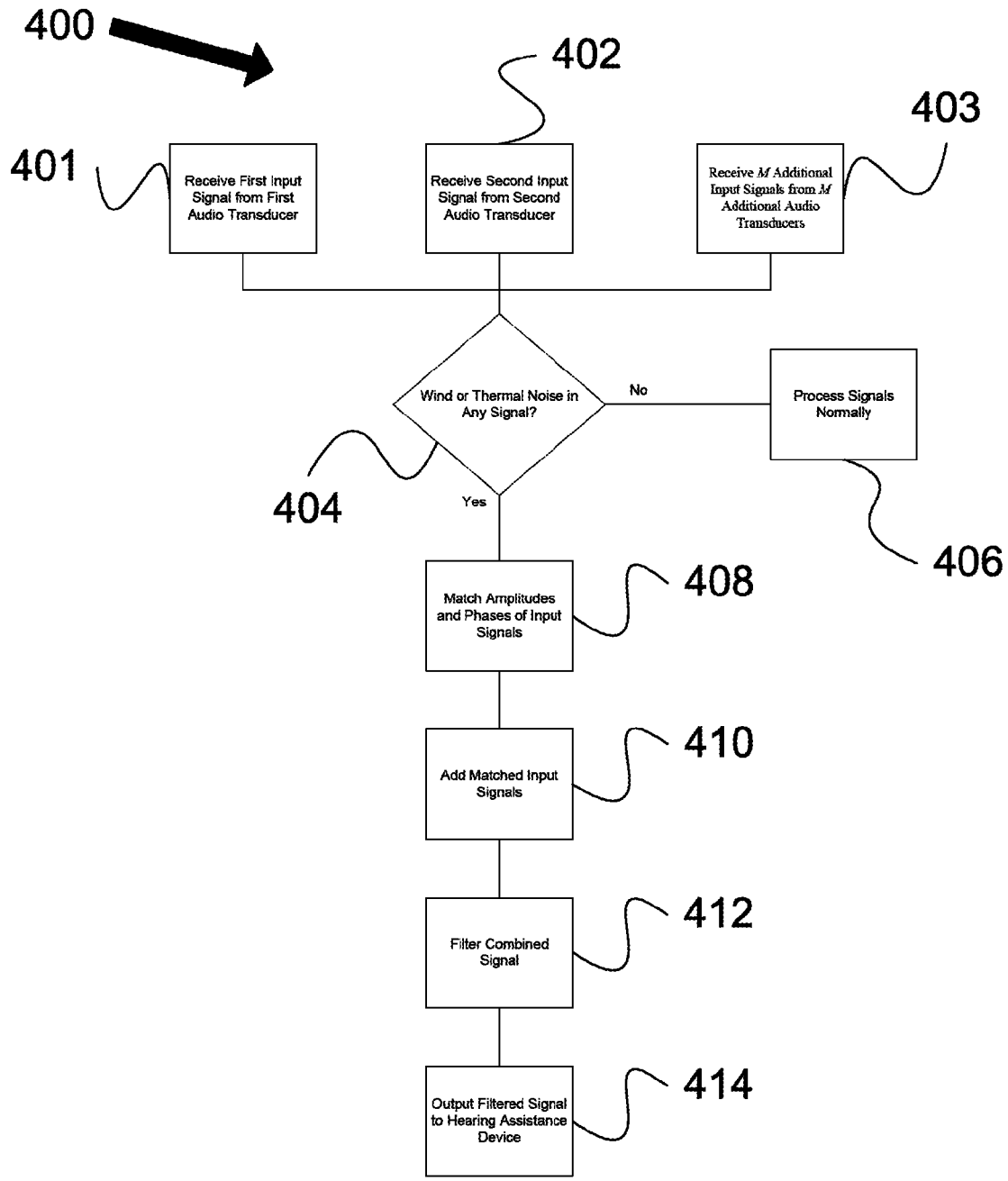
FIG. 4 is an exemplary method for filtering wind noise and/or thermal noise from an audio signal received by a hearing prosthesis according to some embodiments of the present invention.

FIG. 4 illustrates an exemplary method 400 for reducing wind noise and/or thermal noise in an audio signal received by a hearing prosthesis. In blocks 401 and 402, a first input signal is received from a first audio transducer, and a second input signal is received from a second audio transducer, respectively. In the present embodiment, the first audio transducer is closer to a target source than the second audio transducer is. However, in another example the hearing prosthesis includes more than two audio transducers. In this case, M additional input signals are received from M additional audio transducers at block 403, where M is an integer greater than or equal to 1 (one).

Referring to the exemplary method with two input signals, at block 404 both input signals are analyzed for at least one of wind noise and thermal noise. In the present embodiment, at least one of wind noise and/or thermal noise is detected by subtracting the first input signal from the second input signal. The absolute value of the difference in the audio signals is then sent through a low-pass filter, which has the effect of removing non-noise elements from the difference in input signals. If the value of the output filter is above a certain threshold, then it is assumed that at least one of wind noise and thermal noise is present in the signal. However, in alternative embodiments any method suitable for detecting at least one of wind noise and thermal noise in an audio signal is implemented at block 404. In still further embodiments, M additional inputs are analyzed for either wind noise or thermal noise along with the first and second inputs.

Returning to the present embodiment, if neither wind noise nor thermal noise is detected at block 404, then the input signals are processed normally (i.e. using a default mode for signal processing) in block 406. However, if wind noise or thermal noise is detected in block 404, the input signals are processed using delay-sum beamforming.

In block 408, the first input signal and second input signal are filtered to match their amplitudes and phases. In one embodiment, the amplitude and phase responses of the first audio transducer and the second audio transducer are identical. In this example, a time delay is inserted into the first input signal to produce a delayed first input signal. Note, however, that in other embodiments the second audio transducer is closer to the target source than the first audio transducer is. In these alternative embodiments, a time delay is inserted into the second input signal in block 408 to produce a delayed second input signal.

In still further embodiments, whether the first audio transducer or second audio transducer is closer to the target source is determined dynamically. This determination may be based on any number of factors, such as relative amplitude of the peaks in the input signals, arrival time of peaks in the input signals, spatial orientation of the hearing prosthesis, and/or any other factor relevant to determining which audio transducer is closest to the target source. In such embodiments, the time delay is inserted into input signals supplied by the audio transducer closest to the target source. Furthermore, embodiments in which there are more than two audio transducers requires determining which of the first, second, and M additional audio transducers is closest to the target source. In these embodiments, time delays are inserted into all input signals except the input signal received from the audio transducer farthest from the target source.

In yet other examples, the amplitude and phase responses of the first audio transducer and the second audio transducer are not identical. In these embodiments, the amplitudes and the phases of the first input signal and the second input signal are matched using hardware, such as filters, and/or software that employ methods and/or algorithms suitable for matching amplitude and phase responses. Matching the first input signal and the second input signal produces a first matched input signal and a second matched input signal, respectively. However, in some examples at least one of the first audio transducer and the second audio transducer has an amplitude response of 1 (one) and a phase response of 0 (zero). In such examples, at least one of the first input signal and the second input signal is identical to the first matched input signal and the second matched input signal, respectively. Likewise, in examples in which the hearing prosthesis includes more than two audio transducers, M additional input signals are matched in block 408 to produce M additional matched input signals.

In the present embodiment, the delayed first input signal and the second input signal are added in block 410 to produce a combined signal. In examples in which the first input signal and the second input signal are matched, the matched first input signal and the matched second input signal are added in block 410 to produce the combined signal. In alternative examples, the first, second, and M additional matched input signals are added to produce the combined signal.

Returning to the present example, in block 412 band-pass filters are used to reduce both low-frequency and high-frequency noise components in the combined signal. In other embodiments, a high-pass filter is used to reduce the wind noise and/or thermal noise components in the combined signal. In yet other embodiments, the combined signal is passed through an amplitude filter, thereby further reducing the amplitude of wind noise and/or thermal noise in the combined signal. In still other embodiments, a combination of high-pass filters, band-pass filters, amplitude filters, and/or any other filters suitable for removing noise from the combined signal is utilized in block 412. Finally, in block 414, the filtered output signal resulting from block 412 is delivered to additional components of the hearing prosthesis for transmission to the user.

Figure 5:
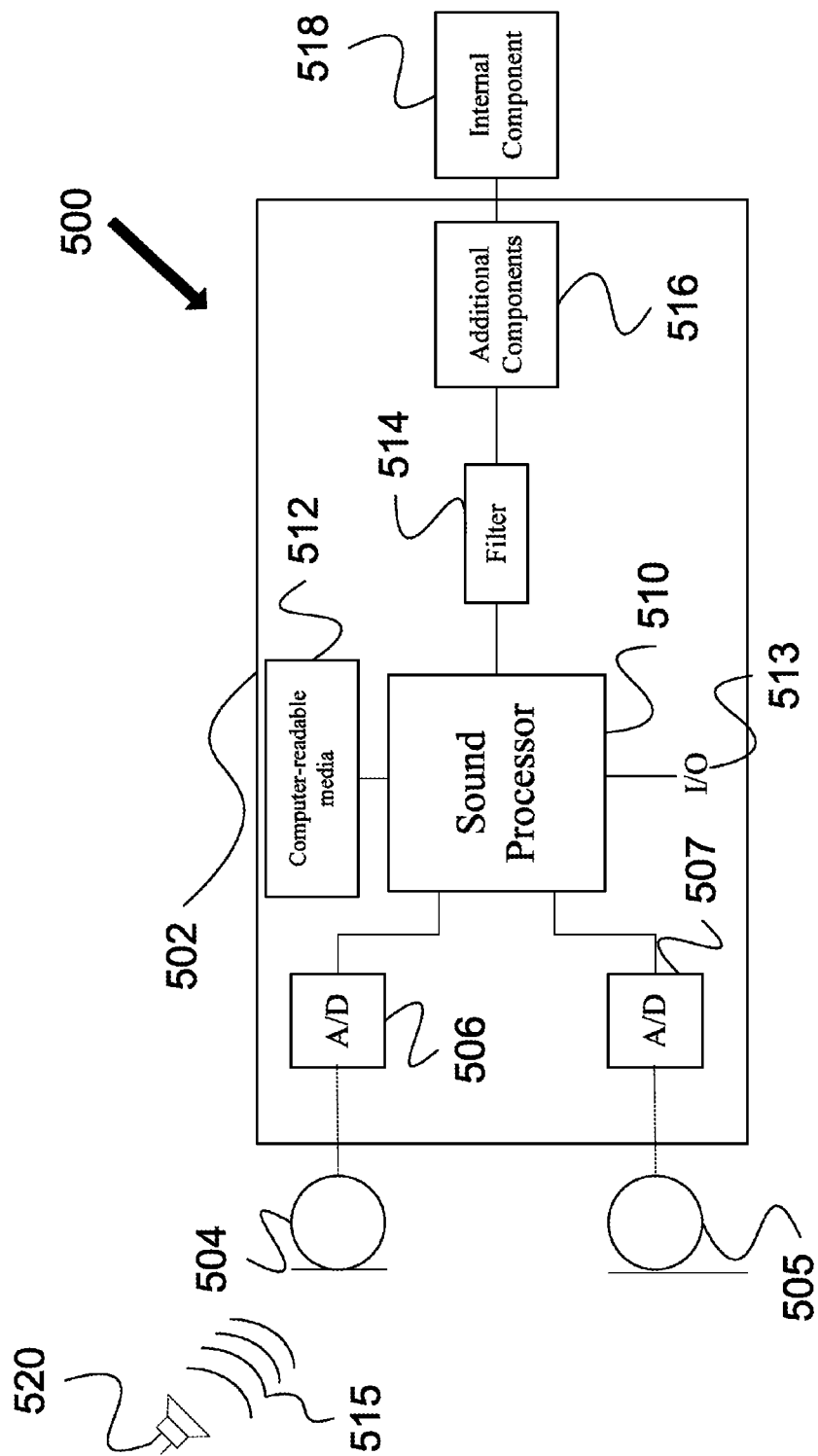
FIG. 5 is a simplified electrical block diagram of one embodiment of a hearing prosthesis according to the present invention.

FIG. 5 illustrates an exemplary simplified block diagram of electrical components necessary for implementing the present invention in a hearing prosthesis 500. In the embodiment shown in FIG. 5, the hearing prosthesis 500 is a cochlear implant comprising a first audio transducer 504, a second audio transducer 505, and an external component 502, such as a behind-the-ear device. In the present embodiment, the first audio transducer 504 and the second audio transducer 505 are omnidirectional microphones. In other embodiments, the hearing prosthesis may be a bone-conduction device, an auditory-brain-stem implant, a direct acoustic stimulation device, or a hearing aid. In these other embodiments, the first audio transducer 504 and the second audio transducer 505 are omnidirectional microphones, directional microphones, electro-mechanical transducers, and/or other audio transducers or combination of audio transducers suitable for use in the type of hearing prosthesis employed. Furthermore, in other embodiments the hearing prosthesis comprises more than two audio transducers.

The external component 502 comprises additional electrical components for implementing the present invention, including a first analog-to-digital converter 506, a second analog-to-digital converter 507, a sound processor 510, a non-transitory computer-readable medium 512, and a filter 514. In some embodiments, the sound processor 510 is a digital signal processor. However, in other embodiments the sound processor 510 is any sound processor suitable for processing audio signals.

In the embodiment depicted in FIG. 5, a target source 520 emits an audio signal 525 that is received by the first audio transducer 504 before the second audio transducer 505. However, in other embodiments the target source may be closer to the second audio transducer, in which case the second audio transducer receives the audio signal before the first audio transducer.

In the illustrated example, the first audio transducer 504 supplies a first input signal to the first analog-to-digital converter 506, and the second audio transducer 505 supplies a second input signal to the second analog-to-digital converter 507. The first analog-to-digital converter 506 then supplies a first digital input signal to the sound processor 510, and the second analog-to-digital converter 507 supplies a second digital input signal to the sound processor 510. However, in some embodiments, the first input signal and the second input signal are supplied directly to the sound processor 510.

The sound processor 510 then implements instructions stored in the non-transitory computer-readable medium 512 necessary to detect the presence of at least one of wind noise and thermal noise in the digital input signals. In this embodiment, the instructions implement the method used to detect wind noise and thermal noise is the difference method described above. However, in other embodiments the sound processor employs any suitable method for detecting the presence of wind noise and/or thermal noise.

If wind noise or thermal noise is detected in either digital input signal, the sound processor 510 utilizes delay-sum beamforming to process the digital input signals. The sound processor 510 implements instructions stored in the non-transitory computer-readable medium 512 for matching the amplitudes and the phases of the first digital input and the second digital input to produce a first matched input signal and a second matched input signal. These instructions comprise, for example, utilizing the amplitude and frequency responses of the first audio transducer 504, the second audio transducer 505, and/or any additional electrical component that has a known amplitude and frequency response to match the amplitudes and the phases of the digital input signals. In some embodiments, the instructions also comprise a time delay associated with the first audio transducer and/or the second audio transducer.

Alternatively, the user of the hearing prosthesis can override the sound processor's determination of whether at least one of wind noise and thermal noise is detected in either digital input signal. In this alternative, the user transmits a request to the sound processor 510 via a user-controlled input device 513, such as a remote computer terminal, to process sounds using delay-sum beamforming. Upon receiving the request from the user-controlled input device 513, the sound processor 510 implements instructions for matching the amplitudes and the phases of the digital input signals irrespective of whether at least one of wind noise and thermal noise is detected in the digital input signals.

In the illustrated embodiment, the sound processor 510 adds the matched digital input signals and outputs a summation signal to the filter 514. The filter 514 comprises high-pass filters, band-pass filters, amplitude filters, and/or any other filters or combination of filters suitable for removing noise from a signal. The filter 514 outputs a filtered signal to additional components 516 of the hearing prosthesis 500 (e.g. for further processing) before being transmitted to an internal component 518 of the hearing prosthesis 500 for further processing and/or delivery to the user. The sound processor 510 returns to its normal mode for processing the digital input signals once at least one of wind noise and thermal noise is no longer detected in at least one of the digital input signals.

Figure 6:
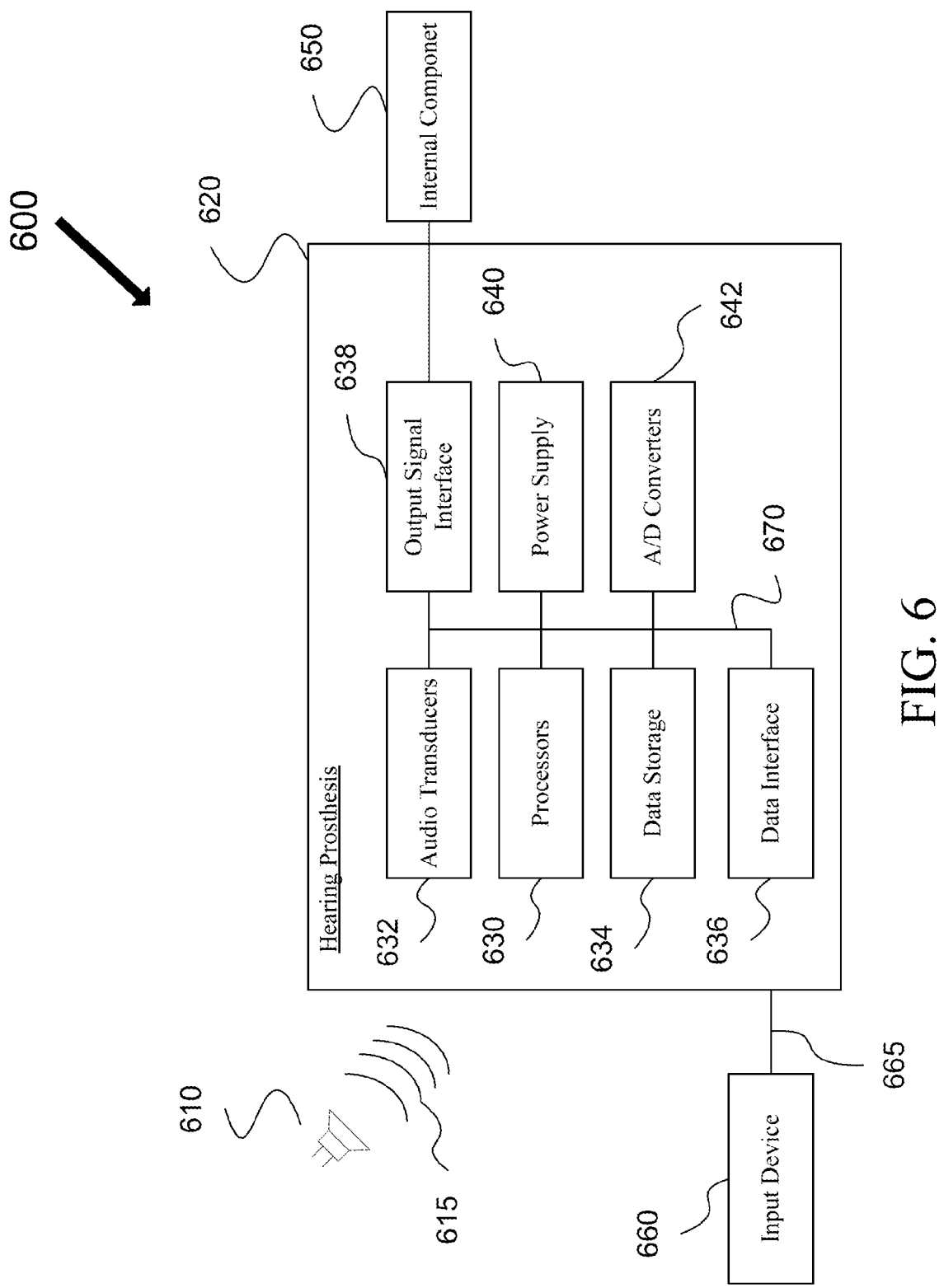
FIG. 6 is a simplified block diagram of a hearing prosthesis system according to an embodiment of the present invention.

FIG. 6 shows one example system 600 that includes a hearing prosthesis 620 configured according to some embodiments of the disclosed methods, systems, and hearing prostheses. In an exemplary embodiment, the hearing prosthesis 620 is a cochlear implant. In other embodiments, the hearing prosthesis 620 is a bone-anchored device, a direct acoustic stimulation device, an auditory-brain-stem implant, an acoustic hearing aid, or any other type of hearing prosthesis configured to assist a prosthesis user in perceiving sound.

The hearing prosthesis 620 illustrated in FIG. 6 includes a data interface 636, at least two audio transducers 632, one or more processors 630, an output signal interface 638, data storage 634, at least one analog-to-digital converter 642, and a power supply 640, all of which are illustrated as being connected directly or indirectly via a system bus or other known circuitry 670.

The power supply 640 supplies power to various components of the hearing prosthesis 620 and can be any suitable power supply, such as a non-rechargeable or rechargeable battery. In one example, the power supply 640 is a battery that can be recharged wirelessly, such as through inductive charging. Such a wirelessly rechargeable battery would facilitate complete subcutaneous implantation of the hearing prosthesis 620 to provide a fully implantable prosthesis. A fully implanted hearing prosthesis has the added benefit of enabling the user to engage in activities that expose the user to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient from stigma, imagined or otherwise, associated with use of the prosthesis.

The data storage 634 generally includes any suitable volatile and/or non-volatile storage components. Further, the data storage 634 may include computer-readable program instructions and perhaps additional data. In some embodiments, the data storage 634 stores an amplitude response, a phase response, and at least one time delay associated with each of the at least two audio transducers 632. In other embodiments, the data storage 634 also includes instructions used to perform at least part of the previously disclosed methods and algorithms, such as the methods for detecting wind noise and/or thermal noise and for inserting time delays into input signals.

In other embodiments, at least one analog-to-digital converter receives the at least two input signals from that at least two audio transducers 632 via the system bus or other known circuitry 670. In such embodiments, the one or more processors comprise a digital signal processor or similar processor suitable for processing digital audio signals.

In the illustrated example, the at least two audio transducers 632 are omnidirectional microphones. In alternative embodiments, the at least two audio transducers 632 comprise directional microphone(s), omnidirectional microphone(s), electro-mechanical transducer(s), and/or any other audio transducer(s) or combination of audio transducers suitable for receiving audio signals for the hearing prosthesis utilized. The at least two audio transducers 632 receive, for example, an audio signal 615 from a target source 610 and supply at least two input signals to the one or more processors. In some circumstances, the at least two audio transducers also receive wind noise and/or thermal noise, which is included in the at least two input signals.

In the present example, the one or more processors 630 are configured to detect a presence of at least one of wind noise and thermal noise in the at least two input signals. This is accomplished, for example, by calculating the absolute value of the difference in the at least two input signals as previously discussed. However, in other examples the one or more processors are configured to use any suitable method for detecting the presence of at least one of wind noise and thermal noise.

If the one or more processors 630 do not detect the presence of either wind noise or thermal noise, then the input signals are processed using a normal (or default) mode of operation. However, if the one or more processors 630 detect the presence of either wind noise or thermal noise, the one or more processors 630 implement a delay-sum beamforming mode of operation to process the input signals. The one or more processors 630 match the amplitudes and the phases of the at least two input signals. In some embodiments, the one or more processors 630 utilize the amplitude response, the frequency response, and the time delay associated with each of the at least two audio transducers to match the amplitudes and the phases of the at least two input signals. However, in other examples, the one or more processors 630 employ any method and/or algorithm suitable for matching the amplitudes and the phases of the at least two input signals.

In still other examples, the one or more processors 630 determine which of the at least two input signals requires the insertion of the at least one time delay. This determination is made, for example, by using the previously discussed method for determining which of the at least two audio transducers 632 is closest to the target source 610, though any suitable alternative method may be used.

Once the amplitudes and the phases of the at least two input signals are matched, the one or more processors 630 combine the input signals using an adding algorithm and transmit the summation signal to the output interface 638. The output interface then transmits the summation signal to an internal component 650 for delivery to the user of the hearing prosthesis 620. The one or more processors 630 return to the normal mode for processing the input signals as soon as the processor(s) no longer detect either wind noise or thermal noise.

In some situations, the user requests that audio signals be processed using delay-sum beamforming. In such cases, the user initiates a request from an input/output device 660. The input/output device 660 is, for example, a remote computer terminal suitable for issuing instructions to the one or more processors. The input/output device 660 transmits the request to the data interface 636 via a communication connection 665. The communication connection 665 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, and the like.

The data interface 636 transmits the request to the one or more processors 630. Upon receiving the request, the one or more processors matches the amplitudes and the phases of the at least two input signals regardless of whether at least one of wind noise and thermal noise is detected. The one or more processors continue to process the at least two input signals in this manner until the user transmits a request via the input/output device 660 to return to normal (or default) signal processing.

Various modifications can be made to the hearing prosthesis 620 illustrated in FIG. 6. For example, the hearing prosthesis 620 may include additional or fewer components arranged in any suitable manner. In some examples, the hearing prosthesis 620 includes other components to process external audio signals, such as components that measure vibration in the skull caused by audio signals and/or components that measure electrical output of portions of a person's hearing system in response to audio signals. Further, depending on the type and design of the hearing prosthesis 620, the illustrated components may be enclosed within a single operational unit or distributed across multiple operational units (e.g., two or more internal units or an external unit and an internal unit).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   receiving a first audio input signal from a first audio transducer, wherein the first audio input signal has an amplitude and a phase;
   receiving at least one additional audio input signal from at least one additional audio transducer, wherein the at least one additional audio input signal has an amplitude and a phase;
   detecting at least one of wind noise or thermal noise in at least one of the first audio input signal or the at least one additional audio input signal; and
   using delay-sum beamforming to reduce at least one of wind noise or thermal noise in at least one of the first audio input signal or the at least one additional audio input signal, wherein using delay-sum beamforming includes:
      determining whether to apply a time delay to the first audio input signal or the at least one additional audio input signal,
      matching the amplitude of the first audio input signal and matching the phase of the first audio input signal to produce a first matched audio input signal,
      matching the amplitude of the at least one additional input signal and matching the phase of the at least one additional input signal to produce at least one additional matched audio input signal,
      adding the first matched audio input signal and the at least one additional matched audio input signal to produce an output signal, and
      transmitting the output signal to an output component of a hearing prosthesis.

2. The method of claim 1, wherein matching the amplitudes and the phases of the first audio input signal and the at least one additional audio input signal is based in part on an amplitude response and a phase response of the first audio transducer and an amplitude response and a phase response of the at least one additional audio transducer.

3. A method comprising:
   receiving a first audio input signal from a first audio transducer, wherein the first audio input signal has an amplitude and a phase;
   receiving at least one additional audio input signal from at least one additional audio transducer, wherein the at least one additional audio input signal has an amplitude and a phase;
   detecting at least one of wind noise or thermal noise in at least one of the first audio input signal or the at least one additional audio input signal; and
   using delay-sum beamforminq to reduce at least one of wind noise or thermal noise in at least one of the first audio input signal and the at least one additional audio input signal, wherein using delay-sum beamforminq includes determining whether to apply a time delay to the first audio input signal or the at least one additional audio input signal, and wherein determining whether to apply the time delay to the first audio input signal or the at least one additional audio input signal comprises determining which of the first audio transducer and the at least one additional audio transducer is closer to a target source.

4. The method of claim 3, wherein, upon determining that the first audio transducer is closer to the target source than the at least one additional audio transducer and upon detecting at least one of wind noise or thermal noise in at least one of the first audio input signal or the at least one additional audio input signal, the method further comprises:
   applying the time delay to the first audio input signal to produce a delayed first audio input signal; and
   matching the amplitudes and the phases of the delayed first audio input signal and the at least one additional input signal to produce a first matched audio input signal and at least one additional matched audio input signal, respectively.

5. The method of claim 3, wherein, upon determining that the at least one additional audio transducer is closer to the target source than the first audio transducer and upon detecting at least one of wind noise or thermal noise in at least one of the first audio input signal or the at least one additional audio input signal, the method further comprises:
   applying the time delay to the at least one additional audio input signal to produce a delayed at least one additional audio input signal; and
   matching the amplitudes and the phases of the first audio input signal and the delayed at least one additional audio input signal to produce a first matched audio input signal and at least one additional matched audio input signal, respectively.

6. The method of claim 1, wherein one of the first matched audio input signal or the at least one additional audio matched input signal is equivalent to one of the first audio input signal or the at least one additional audio input signal, respectively.

7. A system comprising:
   a user-controlled input/output device configured to receive a user-initiated request;
   at least two audio transducers configured to generate at least two input signals that include information indicative of a sound, wherein each the at least two audio transducers generates one of the at least two input signals; and
   one or more processors configured to:
      detect a presence of at least one of wind noise or thermal noise in at least one of the at least two input signals;

in response to detecting the presence of at least one of wind noise or thermal noise, generate a summation signal by:
- applying at least one time delay to one or more of the at least two input signals,
- matching amplitudes and phases of the at least two input signals to produce at least two matched input signals if at least one of wind noise or thermal noise is detected, and
- adding the at least two matched input signals to produce the summation signal;

receive a request signal from the user-controlled input/output device that includes information indicative of the user-initiated request;

in response to receiving the request signal, generate the summation signal regardless of whether at least one of wind noise or thermal noise is detected in at least one of the at least two input signals; and output the summation signal to a component of a hearing prosthesis.

8. The system of claim 7, wherein the one or more processors comprise a digital signal processor.

9. The system of claim 8, wherein the system further comprises at least one analog-to-digital converter, wherein the at least two input signals are analog signals, and wherein the at least one analog-to-digital converter digitizes the at least two input signals.

10. The system of claim 7, wherein at least one of the at least two input signals has the same amplitude and phase as one of the at least two matched input signals.

11. A hearing prosthesis comprising:
- two or more audio transducers; and
- at least one sound processor, wherein the at least one sound processor is configured to improve the signal-to-noise ratio of audio signals supplied by the two or more audio transducers by utilizing delay-sum beamforming upon detecting at least one of wind noise or thermal noise in the audio signals, wherein utilizing delay-sum beamforming includes determining which of the two or more audio transducers is a reference audio transducer that is farthest from a source of a sound included in that audio signals.

12. The hearing prosthesis of claim 11, wherein an amplitude response and a phase response are associated with each of the two or more audio transducers, and wherein a time delay is associated with each of the two or more audio transducers other than the reference audio transducer.

13. The hearing prosthesis of claim 11, wherein at least one of the two or more audio transducers has an amplitude response and a phase response that results in a matched audio signal being approximately equivalent to the audio signal from which the matched audio signal is determined.

14. The hearing prosthesis of claim 11 further comprising at least one output component, wherein, to utilize delay-sum beamforming, the at least one sound processor is further configured to:
- match amplitudes and phases of the audio input signals supplied by the two or more audio transducers to produce matched audio input signals;
- add the matched audio input signals to produce an output signal; and
- transmit the output signal to the at least one output component.

15. The hearing prosthesis of claim 11 further comprising an interface configured to receive a request from a user input device indicating that delay-sum beamforming be utilized to process audio input signals, wherein the at least one sound processor is further configured to:
- receive the request from the interface; and
- process the audio input signals supplied by the two or more audio transducers utilizing delay-sum beamforming upon receiving the request from the user input device irrespective of whether the at least on sound processor detects at least one of wind noise or thermal noise in the audio signals.

16. The hearing prosthesis of claim 11, wherein the at least one sound processor comprises a digital signal processor.

17. The hearing prosthesis of claim 16 further comprising at least one analog-to-digital converter, wherein the at least one analog-to-digital converter digitizes the audio input signals supplied by the two or more audio transducers and supplies the digitized audio input signals to the at least one sound processor.

18. The hearing prosthesis of claim 11, wherein the hearing prosthesis comprises components configured for use in at least one of the following: a cochlear implant, a bone-conduction device, a direct acoustic stimulation device, an auditory-brain-stem implant, or an acoustic hearing aid.

19. The hearing prosthesis of claim 11, wherein the two or more audio transducers are omnidirectional microphones.

* * * * *